(12) United States Patent
Bachand et al.

(10) Patent No.: US 6,464,939 B1
(45) Date of Patent: Oct. 15, 2002

(54) SALIVA TESTING AND CONFIRMATION DEVICE

(75) Inventors: Steven S. Bachand, Laguna Niguel, CA (US); Geoffrey R. Anderson, Lakewood, CA (US); Lawrence C. McPhee, Irvine, CA (US); Stephen K. Schultheis, Laguna Hills, CA (US); Dennis D. Blevins, Laguna Hills, CA (US); John A. Faux, Lake Forest, CA (US)

(73) Assignee: Varian, Inc., Palo Alto, CA (US)

( * ) Notice: Subject to any disclaimer, the term of this patent is extended or adjusted under 35 U.S.C. 154(b) by 132 days.

(21) Appl. No.: 09/610,818

(22) Filed: Jul. 6, 2000

(51) Int. Cl.[7] ............................................... G01N 21/00
(52) U.S. Cl. ............................ 422/58; 422/55; 422/56; 422/61; 436/174; 600/572; 600/573
(58) Field of Search ............................... 422/58, 55, 56, 422/61, 99, 100, 102, 81; 436/165, 518, 174, 180; 600/572, 573, 575, 585; 604/1, 2; 206/269

(56) References Cited

U.S. PATENT DOCUMENTS

| | | | |
|---|---|---|---|
| 4,418,702 A | 12/1983 | Brown et al. | 128/760 |
| 4,580,577 A | 4/1986 | O'Brien et al. | 128/760 |
| 4,834,706 A | 5/1989 | Beck et al. | 604/111 |
| 5,268,148 A | 12/1993 | Seymour | 422/101 |
| 5,647,849 A * | 7/1997 | Kalin | 604/111 |
| 5,766,962 A * | 6/1998 | Child et al. | 436/518 |
| 5,830,410 A | 11/1998 | Thieme et al. | 422/58 |

* cited by examiner

Primary Examiner—Jill Warden
Assistant Examiner—Sam Siefke
(74) Attorney, Agent, or Firm—Walter A. Hackler

(57) ABSTRACT

A saliva testing and confirmation device generally includes an expresser cup adapted to receive and compress a foam collection swab capable of absorbing a fluid specimen such as saliva. The device also includes a testing and confirmation platform integral with the expresser cup. A channel or groove in the cup is provided for directing a flow of expressed fluid from the expresser into both a test well and a confirmation well. A lateral flow reagent test strip, in fluid communication with the test well may be encased in the platform and partially revealed for analysis of test results. The confirmation well includes a fluid tight cap having a tamper evident seal.

28 Claims, 3 Drawing Sheets

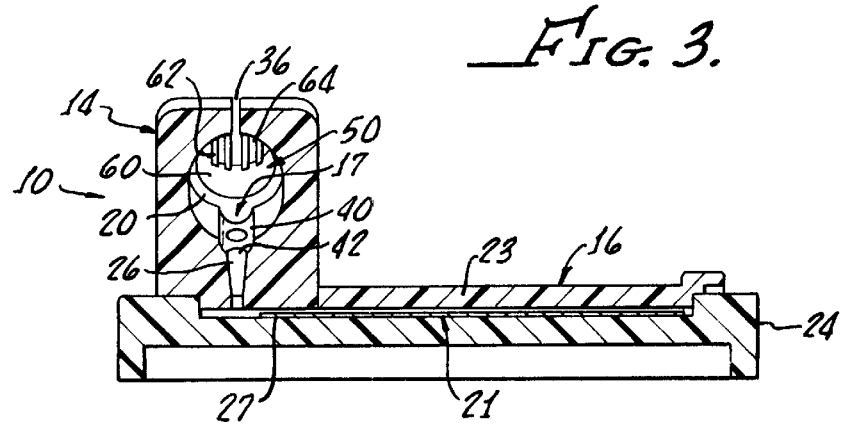
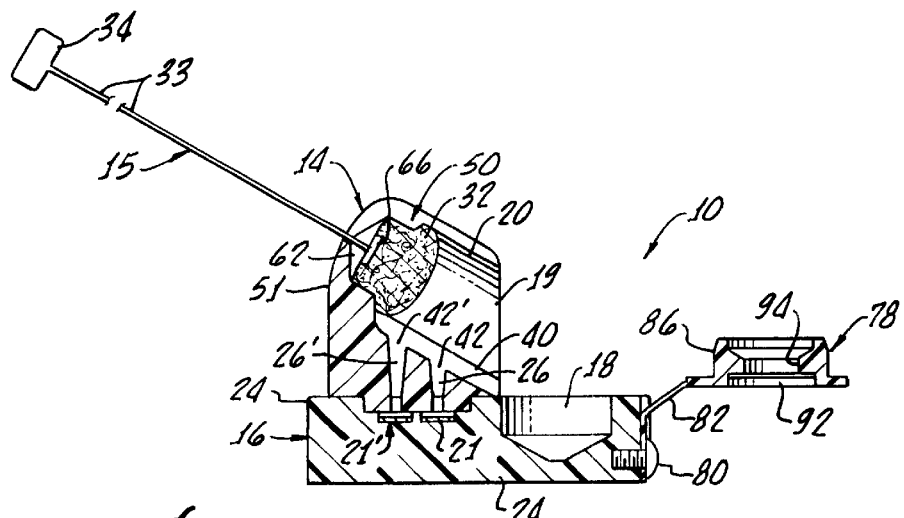
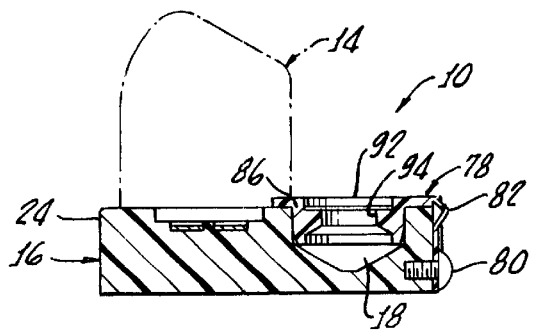

SALIVA TESTING AND CONFIRMATION DEVICE

The present invention generally relates to fluid specimen collection and testing devices, and more specifically relates to an oral fluid or saliva collection, testing and confirmation device.

Unlike other forms of fluid specimens such as blood or urine, collection and analysis of oral fluid, for example saliva, for diagnostic purposes is complicated by many factors, for example, the low volumes of salivary fluid secreted, the relatively high viscosity of the fluid, and the diverse anatomic dispersion of the salivary glands. These problems become compounded when a single saliva sample is to be divided into two or more portions as is sometimes desired. Most techniques for collection involve the use of capillary tubes, suction into micro pipettes, chewing on paraffin, and/or aspiration from the mouth into polypropylene syringes.

In addition, testing of salivary specimens has not yet been extensively developed. Blood and urine samples have for long been the primary fluids used for testing for disease as well as for evidence of substance abuse. However, it is now known that human saliva carries lymphocytes, plasma cells and immunoglobulins that are directly related to the immunoglobulins found in the blood. In addition, saliva carries immunoglobins that are believed to be peculiar to saliva, for example, the antibody known as secretory IgA.

Because of the association between immunoglobulins of the blood and saliva, as well as the occurrence of secretory IgA, antigen-antibody tests have been conducted on salivary fluid to assess the value of such tests as screening tools for disease. Saliva sampling kits have been developed for HIV laboratory testing. As a result of a joint effort between corporations Epitope, Inc., STC Technologies Inc., and LabOne, Inc., a laboratory saliva drug testing system called "Intercept" has been developed and marketed. The "Intercept" system uses a saliva sample collected in the field.

U.S. Pat. No. 5,933,614 to Cesarczyk describes a Sample Collection Method with Extraction Sleeve. The device is designed for collecting saliva or urine samples using an absorbent, elongate foam member secured within a hollow tube and having a portion extending therefrom. The foam member is used to absorb a fluid specimen. The foam member and hollow tube are slidably mounted within an outer sleeve covering the foam member. Fluid is collected by a user exerting pressure against the sleeve to compress the foam member and thereby release the fluid. According to Cesarczyk, the device provides an aseptic, easy to use device for collecting a fluid sample such as saliva.

The present invention exemplifies an improved oral fluid collection device which is easier to use than other devices in the field than those presently available.

The present invention provides an improved sampling device for collecting and delivering an oral fluid specimen such as saliva, for diagnostic testing. The invention further provides an improved testing and sampling device that allows tamper evident containment of a confirmation sample of a fluid specimen being tested.

SUMMARY OF THE INVENTION

Accordingly, a device is provided for both collecting, testing and confirming a fluid sample, such as blood, urine or saliva and other forms of oral fluid in diagnostic procedures. It is noted that the device is especially advantageous for fluid samples of which only a low volume of sample is available for collection, specifically saliva. It is also advantageous for testing of fluid specimens for presence of abused substances, as it provides a highly reliable means of containing a portion of the fluid specimen under tamper evident seal that is accessible for later confirmation of test results.

The device generally comprises an expresser, including a generally cup-shaped member having a distal opening adapted to receive a fluid collection swab. The fluid collection swab may comprise a foam, sponge or other absorbent member that may be used to collect a sample of fluid specimen by being placed in contact with a supply of the fluid specimen and said fluid specimen being absorbed thereby. In accordance with a preferred embodiment of the device, the expresser provides means for expressing at least a portion of the fluid specimen from the swab when the swab is passed into the generally cup-shaped member. For example, the expresser may include a narrowing port providing means for compressing the absorbent member to effect expression of the fluid specimen therefrom when the fluid saturated swab is pushed or pulled into the port.

Importantly, the device further comprises a testing and confirmation platform fixed to the expresser. The platform provides both testing means for testing a portion of the fluid specimen and confirmation means for storing a portion of the fluid specimen for later testing or confirmation. For example, a test well is provided for receiving a portion of the expressed fluid specimen and directing the portion to a lateral flow reagent strip encased within the platform. The platform further includes at least one window for enabling viewing of a portion of the test strip for determination of test results. The confirmation means may comprise a sealable confirmation well adjacent the expresser distal opening.

A groove or channel, disposed between the expresser and the platform provides means for receiving the fluid from the expresser and channeling the fluid into the testing means and the confirmation well. In one advantageous embodiment of the invention, the test well is sized to contain only enough fluid sample to enable the test to run to completion. Any overflow fluid is channeled past the filled test well and is collected in the confirmation well.

The device in accordance with the invention may be adapted to enable a plurality of tests to be conducted on a single sample of fluid specimen. More specifically, a plurality of test strips, for example two test strips, may be provided in the platform. Accordingly, a plurality of test wells each having a separate inlet for capturing a portion of the fluid sample flowing along the channel, and a plurality of windows for revealing a relevant portion of each test strip, are provided in this embodiment.

One important feature of the present invention is a cap providing tamper evident means for sealing the confirmation well. In a preferred embodiment of the invention, the cap means includes a plug, adapted to engage the confirmation well and including a generally conical portion providing means for locking the cap into engagement with the confirmation well.

BRIEF DESCRIPTION OF THE DRAWINGS

The present invention will be more clearly understood with respect to the following detailed description when considered in conjunction with the appended drawings of which:

FIG. 3 shows a cross sectional view of the device taken along lines 3—3 of FIG. 2;

FIG. 4 shows a cross sectional view of another embodiment of the invention similar to the embodiment shown in FIG. 1–3, including a specimen collection swab partially compressed within the expresser, and including two test strip elements, each test strip element being encased within the testing/confirmation platform and in fluid communication with the expresser;

FIG. 7 shows a partial cross sectional view of the device, similar to the view shown in FIG. 4, in which the confirmation well has been sealed by a locking cap with a puncturable membrane.

DETAILED DESCRIPTION OF THE INVENTION

Figure 1:
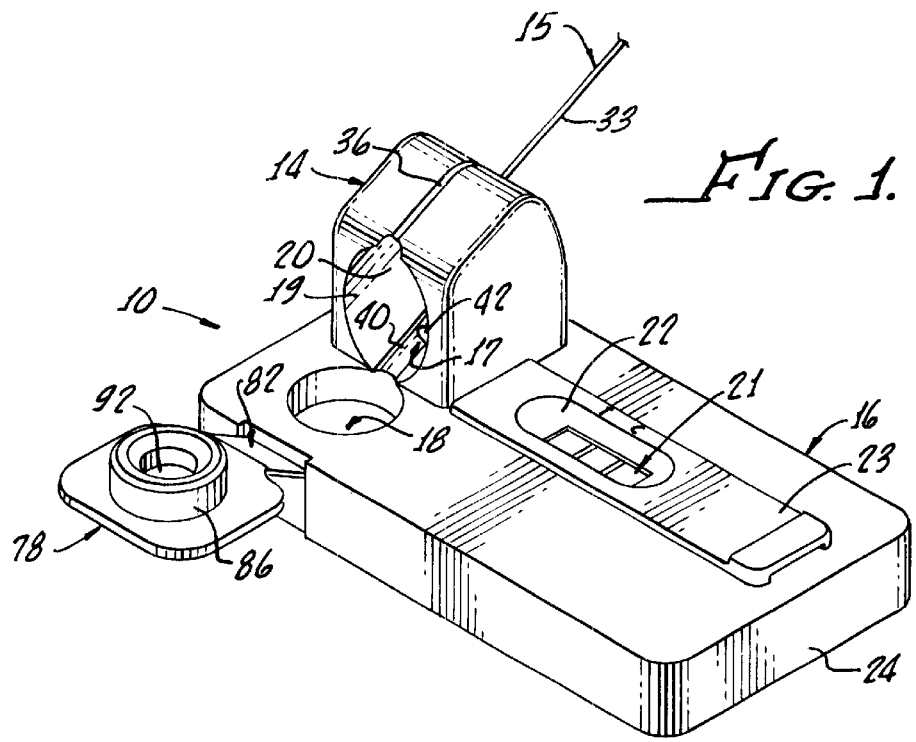
FIG. 1 shows a perspective view of a fluid specimen testing and confirmation device in accordance with the invention, the device including a fluid collection expresser and a testing and confirmation platform having a confirmation well molded therein.
Figure 2:
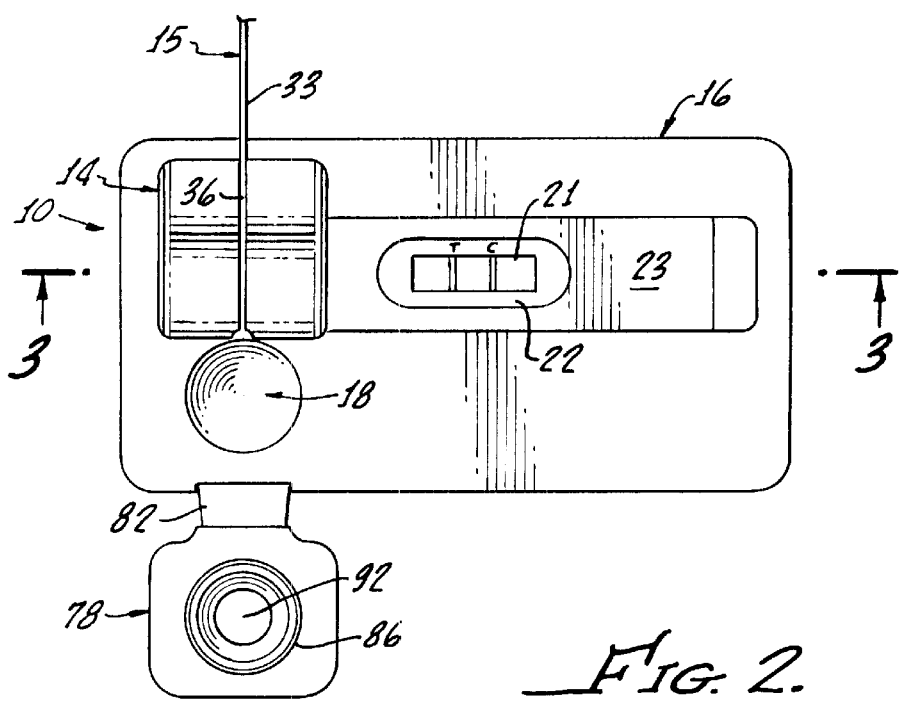
FIG. 2 shows a top view of the device shown in FIG. 1.

Turning now to FIGS. 1 and 2, a fluid specimen collection, testing and confirmation device 10 is shown. The device 10 is particularly useful for testing procedures on saliva and other forms of oral fluid, although with appropriate modification, it may be used for testing procedures on blood, blood components, urine and other fluid specimens, and such modifications if any, are to be considered within the scope of the present invention.

The device 10 generally comprises an expresser 14 which provides means for expressing a fluid specimen from a fluid collection element 15 and a platform 16 connected to the expresser means 14. The device 10 additionally comprises test means 17 (not shown in FIG. 2) for enabling testing of a portion of the fluid specimen. The device 10 further comprises means for collecting a confirmation portion of the fluid specimen. More specifically, the means for collecting the confirmation portion preferably comprises a well 18, hereinafter referred to as a confirmation well 18, disposed in the platform 16.

Referring now specifically to FIG. 1, the expresser means 14 includes a distal opening 19 and an inner port 20, the opening 19 and port 20 being sized and structured to receive the fluid collection element 15. For example, the expresser 14 may be a substantially cup-shaped member as shown.

The platform 16 is adapted to receive at least one test element 21. The test element 21 may comprise, for example, a nitrocellulose lateral flow reagent test strip suitable for performing a desired test on the fluid specimen collected on the collection element 15. The test element 21 is at least partially revealed and visually exposed through at least one window 22 defined in the platform 16, enabling viewing and analysis of test results.

Both the expresser means 14 and the platform 16 may be molded of plastic or other suitable material. The platform 16 may comprise a cover 23 and a base 24, with the test element 21 being fixed therebetween. The expresser means 14 is preferably not manually separable from the platform 16. For example, the expresser means 14 may be integrally molded with the platform cover 23.

Importantly, both the test means 17 and the confirmation means 18, are in fluid communication with the expresser means 14. Turning now to FIG. 3, the test means 17 may include at least one test well 26 that provides fluid communication between the expresser means 14 and a sample portion 27 (i.e. fluid introduction portion) of the test element 21.

FIG. 4 shows an example of the fluid collection element 15 received in an expresser having a plurality of test wells 26, 26', specifically two test wells 26, 26'. As shown, the collection element 15 may include an absorbent swab 32 made of a sponge, foam or other absorbent material. A tether 33, for example a flexible, plastic monofilament including a handle 34, may threaded through the swab 32, to provide means for facilitating manual handling of the swab 32.

Preferably, the expresser means 14 includes a slot 36 (shown in FIGS. 1, 2, 3 and 5) for accommodating the tether 33. This structure facilitates sanitary handling of the collection element 15 by enabling the swab 32 to be manually pulled by the tether 33 into the expresser port 20.

It is contemplated that alternative to the slot 36 shown, the tether 33 may be threaded through an aperture in the expresser means 14, the aperture being generally aligned with the port 20.

Initial collection of a fluid specimen on the swab 32 may be performed as follows. The swab 32, which is preferably clean and sterile, is handled by the tether 33 and placed in the mouth of a patient or subject person. The swab 32 is allowed to remain in the mouth for a time period that is sufficient to allow a sample of saliva fluid to be absorbed thereby. The time period for absorption will generally vary according to the particular subject person and the type of swab material used.

The expresser means 14 is designed to enable sanitary, effective expression of at least a portion of the fluid sample that has been absorbed by the swab 32 in an amount sufficient for both testing and collection. More particularly, after the swab 32 has been substantially saturated with the fluid specimen as described hereinabove, the swab 32 is inserted in the expresser port 20. This is easily accomplished by first placing the swab 32 adjacent the expresser distal opening 19, and aligning the tether 33 with the slot 36, and next sliding the tether into the slot 36. By pulling the tether 36 rearward, the swab 32 will be caused to enter the port 20. Alternatively, the swab 32 may is pushed or otherwise drawn into the port 20, for example if no tether 33 is provided.

The expresser port 20 is sized and shaped to cause compression of the swab 32 as the swab 32 is drawn deeper into the port 20. Compression of the swab 32 by the expresser 14 causes a substantial portion of the fluid specimen to be released, or expressed, from the swab 32. The expressed fluid specimen is then directed into the testing means 17 and collected by the confirmation means 18.

More particularly, referring now to FIGS. 1 and 3, the expresser means 14 preferably further comprises channel means 40 for channeling the expressed fluid from the compressed swab 32 to both the test means 17. and the confirmation means 18. For example, an inlet 42 of the test well 26 is defined in the channel means 40, the inlet 42 being suitably sized and positioned to capture the (testing) portion of the expressed fluid as the fluid is channeled toward the confirmation well 18. In the embodiment 10 shown, the channel means 40 comprises a groove, wherein the groove extends substantially along a length of the expresser port 20. Alternatively, the channel means 40 may comprise a downwardly sloped, lower surface of the expresser port 20.

Additionally, as shown most clearly in FIG. 4, the expresser port 20 may have a relatively narrow portion, or cavity 50, which provides means for compressing and holding the swab 32 in a compressed position. The cavity 50 has a size and shape sufficient to cause substantial compression of the swab 32 when the swab 32 is saturated with the fluid specimen. For example, the cavity 50 is substantially smaller in width than a width of the swab 32 in an expanded saturated state. Once the swab 32 has been pulled (or pushed) into the port cavity 50, the swab 32 can be maintained in the compressed position. Holding the swab 32 in the compressed position is important to prevent the swab 32 from expanding and reabsorbing a viscous or slow flowing fluid specimen, such as saliva, as the fluid specimen is channeled through the port 20.

Figure 5:
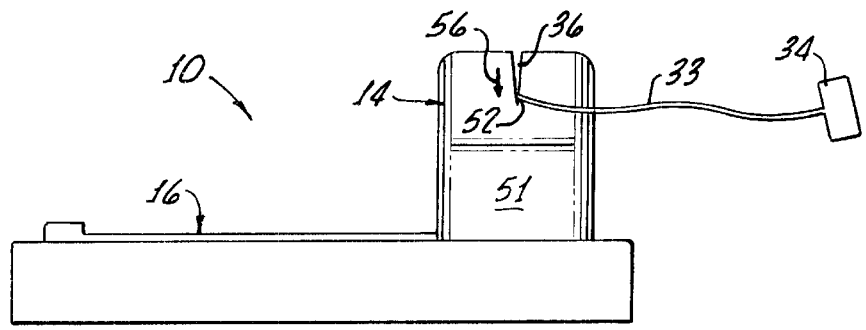
FIG. 5 shows a rear view of the device including a tapered slot for enabling the collection swab to be secured in a compressed position within the expresser.

Turning now as well to FIG. 5, a rear surface 51 of the expresser means 14 is shown with the slot 36 being sufficiently tapered to secure the tether 33 and "lock" the collection element 15 in place. More specifically, the slot 36 may terminate with a "point" or a taper 52 as shown. Accordingly, after the swab 32 has been pulled sufficiently deep into the port 20 such that the swab 32 is being compressed within the port cavity 50 for example, the tether 33 may then be manually pulled toward the slot taper 52, for example in a downward direction (represented by arrow 56) to force the tether 33 into engagement with the slot 36.

These "locking" features, i.e. the narrow cavity 50 and the tapered slot 36, are preferably provided in combination to promote efficiency in testing. For example, these features provide means for enabling a technician or other user of the device 10 to release hold of the collection element 15 and attend to other matters, while the fluid specimen is being expressed from the swab 32, absorbed by the test strip 21, and collected in confirmation well 18. Advantageously, no further manipulation of the device 10 is required after the collection element 15 has been drawn into the port 20 and secured. Multiple tests may be rapidly performed by a single technician using multiple saliva testing and confirmation devices 10 in accordance with the present invention. For particularly viscous fluid specimens such as saliva, which tend to flow relatively slowly, the locking feature is especially advantageous.

Alternative means of expressing fluid from the swab 32 are contemplated. For example, the expresser 14 may be provided with a port having a uniformly conical cross section (not shown) to provide for gradually compressing the swab 32 as a user pulls the swab 32 into the narrowing port. It is also contemplated that the device in accordance with the present invention may include an expresser having manually squeezable walls, such that drops of the fluid may be extracted by a user manually applying pressure to, or squeezing, the expresser. A suitable material for the squeezable expresser is a low density polyethylene plastic.

Referring now back to FIG. 3, means for preventing fluid loss through the slot 36 may be provided. In the embodiment 10 shown for example, a rear surface 60 of the expresser port 20 may be provided with projections, more specifically ribs 62, for preventing expressed fluid from seeping through the tether slot 36 during compression of the swab 32. For example, there may be up to four or more, substantially vertical ribs 62 extending partially down the rear surface 60 of the expresser port 20 and defining open bottom channels 64.

Optionally, a small disk 66 or the like, made for example of rubber or plastic and slidably engaged to the tether 33 as shown in FIG. 4, is provided as further protection against fluid seepage through the slot 36 during compression of the swab 32.

Figure 6:
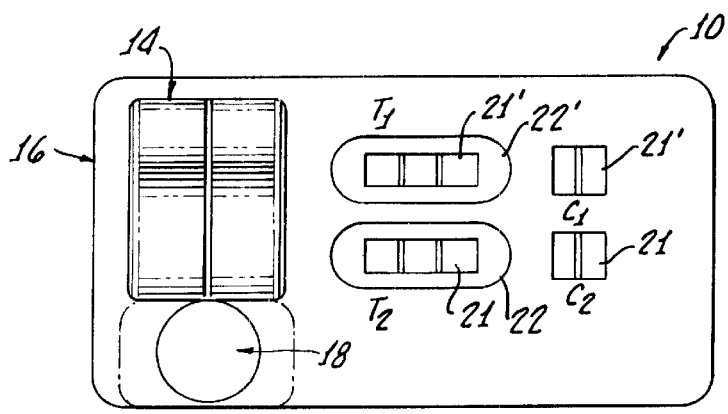
FIG. 6 shows a top view of the embodiment of the device shown in FIG. 4, including two windows for revealing portions of the two test strip elements.

Although only one test element 21 is shown in FIGS. 1 and 2, the device 10 may be modified to allow multiple, different tests to be performed on a single sample of fluid specimen. Such a modification is shown in FIGS. 4 and 6. For example, in accordance with the invention, the testing means 17 may comprise a plurality of test wells 26, 26' with inlets 42, 42' (see FIG. 4), and the platform 16 may be structured to accommodate a plurality of test elements 21, 21', with each element 21, 21' being revealed through one or more windows 22, 22' (see FIG. 6). In the example shown in FIGS. 4 and 6, the saliva testing and confirmation device 10 has been designed to enable two individual tests to be conducted on a sample of fluid expressed from the swab 32.

Referring now to FIGS. 1, 2, 4 and 7, in another advantageous aspect of the invention, means for sealing the confirmation well 18 is provided. More specifically, a molded cap 78 is provided which may be fixed to the platform 16 by a fastener 80 (see FIGS. 4 and 7), or alternatively may be integrally molded thereto. The cap 78 may include a living hinge 82, and may be snap-fitted into the confirmation well 18 after the fluid specimen has been collected in the well 18, thus sealing and preserving the contents for shipment. Even more particularly, the cap 78 may be engageable with the confirmation well 18 by means of depending rim 86 also shown in FIGS. 1 and 2, which will provide a fluid tight seal with the well 18.

As mentioned hereinabove, the expresser means 14 is preferably integrally molded with the platform 16. However, as an optional feature of the invention, the expresser means 14 may be separable from the platform 16. Thus, after the confirmation well 18 has been sealed, the expresser means 14 can be manually snapped off or otherwise removed from the platform 16, and discarded. When closed over the well 18, the cap 78 may form a substantially flush surface with the platform 16. With the expresser 14 removed, the device is less bulky, and test results can be easily photocopied through the platform window 22.

Preferably, the cap 78 is a tamper evident sealing cap 78. For example, the cap 78 may comprise suitable means for snap locking the cap 78 to the confirmation well 18. In addition, the cap 78 preferably includes a puncturable membrane 92 made of foil laminate or other suitable, puncturable material, sealed to a rim 94 of the cap 78. Thus, when the device 10 is ready for confirmation, a lab technician may access the confirmation sample in the sealed confirmation well 18 by penetrating or puncturing the foil laminate 92. The sample then can be removed from the well 18 by pipette for confirmation testing. To facilitate removal by pipette, the confirmation well 18 may be tapered as shown in FIGS. 4 and 7. The tamper evident seal 92 allows for easy access to the sample as well as tamper evidence for chain of custody purposes.

Figure 8:
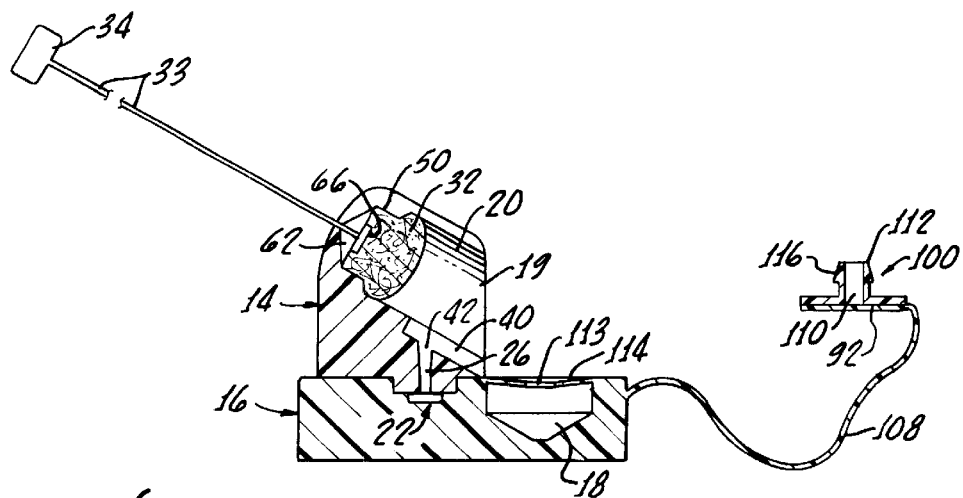
FIG. 8 shows a cross sectional view of the device with an alternative, tamper evident cap for sealing the confirmation well.

An alternative tamper evident sealing cap 100, or "plug", is shown in FIG. 8. This cap 100 is connected to a tether 108 and an open end 110 is sealed using a puncturable membrane 92 made of foil laminate or other suitable puncturable material, and a narrowing, conical portion 112 that is adapted to snap into and lock into engagement with the confirmation well 18 in cooperation with flange 114 and seal stop 116. The plug may be made of any suitable, resilient plastic material.

Although there has been hereinabove described a saliva testing and confirmation device, in accordance with the present invention, for the purpose of illustrating the manner in which the invention may be used to advantage, it will be appreciated that the invention is not limited thereto. For example, although the hereinabove description refers to a device for testing and confirmation of a sample of oral fluid such as saliva, the device is also useful for testing other fluids as well, such as whole blood, blood serum, plasma and urine. Accordingly, any and all modifications, variations, or equivalent arrangements which may occur to those skilled in the art should be considered to be within the scope of the invention as defined in the appended claims.

What is claimed is:

1. A fluid specimen testing device comprising:

expresser means for expressing a fluid specimen from a fluid collection swab;

a platform connected to the expresser means;

testing means, at least partially encased within the platform, for enabling diagnostic testing of a portion of the fluid specimen expressed by the expresser means;

confirmation means, disposed in the platform, for collecting another portion of the fluid specimen expressed by the expresser means; and channel means, for fluidly connecting the expresser means with the testing means and the confirmation means.

wherein the channel means comprises a sloped surface disposed between the expresser and the confirmation means.

2. The device according to claim 1 wherein the confirmation means comprises a confirmation well integral with said platform.

3. The device according to claim 1 further comprising cap means, connected to the platform, for sealing the confirmation means after the another portion has been collected.

4. The device according to claim 3 wherein the cap means includes a tamper evident seal.

5. The device according to claim 4 wherein the tamper evident seal comprises a locking cap and a puncturable membrane.

6. The device according to claim 1 further comprising means for capturing the diagnostic portion of the fluid specimen expressed by the expresser means, the means for capturing including at least one well having an inlet disposed along the channel means.

7. The device according to claim 1 further comprising means for capturing the diagnostic portion of the fluid specimen expressed by the expresser means, the means for capturing including a plurality of wells each having an inlet disposed along the channel means.

8. The device according to claim 6 wherein the channel means comprises a sloped surface of the expresser means.

9. The device according to claim 8 wherein the sloped surface is defined by a groove.

10. The device according to claim 1 wherein the testing means comprises a lateral flow test strip embedded in the platform, and the platform includes window means for enabling viewing of at least a portion of the lateral flow test strip.

11. The device according to claim 1 wherein the expresser means comprises a generally cup shaped member having a distal opening adapted to receive the collection swab and slot means for facilitating manual insertion of the collection swab therein.

12. The device according to claim 1 wherein the expresser means comprises a generally cup shaped member having a distal opening adapted to receive the collection swab and a relatively narrow cavity for compressing the swab as the swab in drawn into the generally cup shaped member.

13. A fluid specimen testing device comprising:

expresser means for expressing a fluid specimen from a fluid specimen collection swab; and a testing and confirmation platform connected to the expresser means, the platform including means for testing the fluid specimen, confirmation means for collecting a portion of the fluid specimen, and channel means for fluidly connecting the expresser means with both the means for testing and the confirmation means, wherein the channel means comprises a sloped surface disposed between the expresser and the confirmation means.

14. The device according to claim 13 wherein the expresser means comprises a generally cup shaped member having a distal opening adapted to receive the fluid specimen collection swab.

15. The device according to claim 13 wherein the expresser means comprises a generally cup shaped member having a distal opening adapted to receive the collection swab and a relatively narrow cavity for compressing the swab as the swab in drawn into the generally cup shaped member.

16. The device according to claim 15 wherein the sloped surface is defined by a groove.

17. The device according to claim 16 wherein the means for testing the fluid specimen includes means for capturing a diagnostic portion of the fluid specimen expressed by the expresser means, the means for capturing the diagnostic portion including at least one test well having an inlet disposed along the sloped surface.

18. The device according to claim 16 wherein the means for testing the fluid specimen includes means for capturing a diagnostic portion of the fluid specimen expressed by the expresser means, the means for capturing the diagnostic portion including a plurality of test wells each having an inlet disposed along the sloped surface.

19. The device according to claim 17 wherein the means for testing further includes a lateral flow reagent test strip encased within the platform and in fluid communication with the at least one test well.

20. The device according to claim 18 wherein the means for testing further includes a plurality of lateral flow reagent test strips encased within the platform and in fluid communication with the plurality of test wells.

21. The device according to claim 13 wherein the confirmation means comprises a confirmation well and cap means for sealing the confirmation well.

22. The device according to claim 21 wherein the cap means includes a tamper evident seal.

23. A fluid specimen testing device comprising:

a collection swab including an absorbent member suitable for collecting a fluid specimen for diagnostic purposes and a tether connected to the absorbent member;

expresser means including a narrow cavity for enabling the fluid specimen collected on the collection swab to be expressed in an amount sufficient for testing and collection; and a testing and confirmation platform integral with the expresser means, the platform including means for testing a diagnostic portion of the fluid specimen and confirmation means for collecting a confirmation portion of the fluid specimen, wherein the expresser means further includes channel means for fluidly connecting the narrow cavity with both the means for testing and the confirmation means; said channel means comprising a sloped surface disposed between the expresser and the confirmation means.

24. The device according to claim 23 wherein the narrow cavity is sized to cause substantial compression of the absorbent member when the absorbent member is drawn therein.

25. The device according to claim 23 wherein the means for testing includes means for capturing the diagnostic portion of the fluid specimen expressed by the expresser means, the means for capturing including at least one test well having an inlet disposed along the channel means.

26. The device according to claim 23 wherein the means for testing includes means for capturing the diagnostic portion of the fluid specimen expressed by the expresser means, the means for capturing including a plurality of test wells, each having an inlet disposed along the channel means.

27. The device according to claim 25 wherein the confirmation means includes a confirmation well disposed downstream of the at least one test well.

28. The device according to claim 26 wherein the expresser means further comprises slot means for allowing passage of the tether, the slot means being sufficiently tapered to secure the tether and lock the collection swab in place while the absorbent member is being compressed within the cavity.

* * * * *